(12) United States Patent
Kleyman et al.

(10) Patent No.: US 9,119,664 B2
(45) Date of Patent: Sep. 1, 2015

(54) INTEGRAL FOAM PORT

(75) Inventors: Gennady Kleyman, Brooklyn, NY (US); Greg Okoniewski, North Haven, CT (US)

(73) Assignee: Covidien LP, Mansfield, MA (US)

(*) Notice: Subject to any disclaimer, the term of this patent is extended or adjusted under 35 U.S.C. 154(b) by 77 days.

(21) Appl. No.: 13/223,700

(22) Filed: Sep. 1, 2011

(65) Prior Publication Data
US 2012/0157784 A1    Jun. 21, 2012

Related U.S. Application Data

(60) Provisional application No. 61/424,748, filed on Dec. 20, 2010.

(51) Int. Cl.
*A61B 1/32* (2006.01)
*A61B 17/34* (2006.01)

(52) U.S. Cl.
CPC .......... *A61B 17/3423* (2013.01); *A61B 17/3462* (2013.01); *A61B 2017/3441* (2013.01); *A61B 2017/3445* (2013.01); *A61B 2017/3464* (2013.01); *A61B 2017/3466* (2013.01)

(58) Field of Classification Search
CPC ........... A61B 17/3423; A61B 17/3445; A61B 2017/3466; A61B 2017/3464; A61B 17/3421; A61B 17/3462; A61B 17/3498; A61B 2017/3445–2017/3449; A61B 2017/347
USPC ........ 600/201–249, 114; 604/167.01, 167.03, 604/167.04, 167.06, 256; 606/185, 108; 128/188
See application file for complete search history.

(56) References Cited

U.S. PATENT DOCUMENTS

| 4,112,932 A | 9/1978 | Chiulli |
| 5,375,588 A | 12/1994 | Yoon |
| 5,385,553 A | 1/1995 | Hart et al. |
| 5,540,648 A | 7/1996 | Yoon |

(Continued)

FOREIGN PATENT DOCUMENTS

| EP | 0538060 A1 | 4/1993 |
| EP | 2044889 A1 | 4/2009 |

(Continued)

OTHER PUBLICATIONS

U.S. Appl. No. 13/091,246, filed Apr. 21, 2011, Paul D. Richard.

(Continued)

*Primary Examiner* — Todd Manahan
*Assistant Examiner* — Marcela I Shirsat

(57) ABSTRACT

A surgical apparatus includes a seal anchor member. The seal anchor member includes a first end, a second end, at least one longitudinal port extending between the two ends, and a seal assembly disposed within the at least one longitudinal port. The seal assembly can be positioned at any location along the length of the at least one longitudinal port. The seal assembly comprises a seal housing which is dimensioned to receive a surgical instrument inserted into the at least one longitudinal port and form a substantially fluid-tight seal therewith. The seal housing may comprise a pivotable member to pivot the surgical instrument inserted therein. The at least one longitudinal port may define two gradually enlarging openings to facilitate the maneuverability of the surgical instrument inserted therein. The at least one longitudinal port may comprise a protective sleeve to protect it from accidental penetration by the surgical instrument.

6 Claims, 6 Drawing Sheets

(56) References Cited

U.S. PATENT DOCUMENTS

| | | | |
|---|---|---|---|
| 5,545,142 A | 8/1996 | Stephens et al. | |
| 5,656,013 A | 8/1997 | Yoon | |
| 5,752,938 A * | 5/1998 | Flatland et al. | 604/167.01 |
| 5,842,971 A | 12/1998 | Yoon | |
| 5,865,807 A | 2/1999 | Blake, III | |
| 5,895,377 A * | 4/1999 | Smith et al. | 604/256 |
| 5,913,847 A | 6/1999 | Yoon | |
| 5,989,228 A | 11/1999 | Danks et al. | |
| 6,086,603 A | 7/2000 | Termin et al. | |
| 6,447,489 B1 | 9/2002 | Peterson | |
| 6,551,270 B1 | 4/2003 | Bimbo et al. | |
| 6,578,577 B2 | 6/2003 | Bonadio et al. | |
| 7,011,314 B2 | 3/2006 | McFarlane | |
| 7,083,626 B2 | 8/2006 | Hart et al. | |
| 7,153,261 B2 | 12/2006 | Wenchell | |
| 7,235,062 B2 | 6/2007 | Brustad | |
| 7,244,244 B2 | 7/2007 | Racenet et al. | |
| 7,344,547 B2 * | 3/2008 | Piskun | 606/185 |
| 7,371,227 B2 | 5/2008 | Zeiner | |
| 7,850,600 B1 * | 12/2010 | Piskun | 600/114 |
| 7,998,068 B2 | 8/2011 | Bonadio et al. | |
| 2005/0119525 A1 * | 6/2005 | Takemoto | 600/114 |
| 2006/0241651 A1 * | 10/2006 | Wilk | 606/108 |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2009/0036745 A1 | 2/2009 | Bonadio et al. | |
| 2009/0093752 A1 | 4/2009 | Richard et al. | |
| 2009/0093850 A1 | 4/2009 | Richard | |
| 2009/0131751 A1 | 5/2009 | Spivey | |
| 2009/0221966 A1 | 9/2009 | Richard | |
| 2009/0221968 A1 | 9/2009 | Morrison et al. | |
| 2009/0227843 A1 | 9/2009 | Smith et al. | |
| 2010/0081995 A1 * | 4/2010 | Widenhouse et al. | 604/164.08 |
| 2010/0100043 A1 | 4/2010 | Racenet | |
| 2010/0113886 A1 * | 5/2010 | Piskun et al. | 600/231 |
| 2010/0228094 A1 | 9/2010 | Ortiz | |
| 2010/0240960 A1 * | 9/2010 | Richard | 600/208 |
| 2010/0249516 A1 * | 9/2010 | Shelton et al. | 600/203 |
| 2010/0268162 A1 * | 10/2010 | Shelton et al. | 604/167.01 |
| 2010/0286484 A1 | 11/2010 | Stellon et al. | |
| 2010/0298646 A1 | 11/2010 | Stellon et al. | |
| 2011/0124970 A1 | 5/2011 | Kleyman | |
| 2011/0125186 A1 | 5/2011 | Fowler et al. | |
| 2011/0251463 A1 | 10/2011 | Kleyman | |
| 2011/0251464 A1 | 10/2011 | Kleyman | |
| 2011/0251465 A1 | 10/2011 | Kleyman | |
| 2011/0251466 A1 | 10/2011 | Kleyman et al. | |

FOREIGN PATENT DOCUMENTS

| | | | |
|---|---|---|---|
| EP | 2098182 A2 | 9/2009 | |
| EP | 2229900 A1 | 9/2010 | |
| EP | 2248478 A1 | 11/2010 | |
| EP | 2253283 A1 | 11/2010 | |
| GB | 2469083 A | 10/2010 | |
| WO | WO 94/04067 A1 | 3/1994 | |
| WO | WO 2006/110733 A2 | 10/2006 | |
| WO | WO 2008/093313 A1 | 8/2008 | |
| WO | WO 2008/121294 A1 | 10/2008 | |
| WO | WO2009/036343 A1 | 3/2009 | |

OTHER PUBLICATIONS

U.S. Appl. No. 13/031,352, filed Feb. 21, 2011, Gennady Kleyman.
U.S. Appl. No. 13/193,647, filed Jul. 29, 2011, Russell Pribanic.
U.S. Appl. No. 13/217,717, filed Aug. 25, 2011, Joshua Stopek.
U.S. Appl. No. 13/221,062, filed Aug. 30, 2011, Gregory Okoniewski.
U.S. Appl. No. 13/223,029, filed Sep. 1, 2011, Michael Davis.
U.S. Appl. No. 13/223,330, filed Sep. 1, 2011, Gregory Okoniewski.
U.S. Appl. No. 13/223,336, filed Sep. 1, 2011, Michael Davis.
U.S. Appl. No. 13/223,613, filed Sep. 1, 2011, Greg Fischvogt.
U.S. Appl. No. 13/223,627, filed Sep. 1, 2011, Gregory Okoniewski.
U.S. Appl. No. 13/223,645, filed Sep. 1, 2011, Gennady Kleyman.
U.S. Appl. No. 13/223,659, filed Sep. 2, 2011, Francesco Alfieri.
U.S. Appl. No. 13/223,678, filed Sep. 1, 2011, Gregory Okoniewski.
U.S. Appl. No. 13/223,700, filed Sep. 1, 2011, Gennady Kleyman.
U.S. Appl. No. 13/224,353, filed Sep. 2, 2011, Gennady Kleyman.
U.S. Appl. No. 13/224,354, filed Sep. 2, 2011, Greg Okoniewski.
U.S. Appl. No. 13/224,355, filed Sep. 2, 2011, Anibal Rodrigues, Jr.
U.S. Appl. No. 13/224,358, filed Sep. 2, 2011, Andrew Barnes.
U.S. Appl. No. 13/228,937, filed Sep. 9, 2011, Dino Kasvikis.
U.S. Appl. No. 13/228,960, filed Sep. 9, 2011, Russell Pribanic.
European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search report for corresponding EP11194221 date of mailing is Jun. 11, 2012 (11 pgs).

* cited by examiner

INTEGRAL FOAM PORT

CROSS REFERENCE TO RELATED APPLICATIONS

The present application claims the benefit of and priority to U.S. Provisional Patent Application Ser. No. 61/424,748 filed on Dec. 20, 2010, the entire contents of which are incorporated herein by reference.

BACKGROUND

1. Technical Field

The present disclosure relates generally to surgical portals for use in minimally invasive surgical procedures, such as endoscopic and/or laparoscopic procedures, and more particularly, relates to a surgical portal that allows multiple surgical instruments to be inserted through a single incision.

2. Description of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site.

To this end, various access devices with sealing features are used during the course of minimally invasive procedures to provide an access for surgical objects to enter the patient's body. Generally, an access device is made of resilient material and has one or more ports, and each port is designed to accommodate one surgical object to be inserted therethrough. In the prior art, when a surgical object advances through a port, the resilient material is adapted to frictionally engage the surgical object, thus forming a seal between the surgical object and the port along the length of the port.

Further, in the prior art, each port is open-ended. Therefore, before the insertion of surgical objects through the open-ended ports, the insufflation gas may escape from the patient's body cavity through the open-ended ports. For the same reason, foreign matter may inadvertently enter into the patient's body cavity through the open-ended ports. To overcome this problem, cannula assemblies have been used heretofore to couple with the prior access devices together providing a sealed passage for the surgical objects to access the patient's body. A cannula is a tubular member that is positioned within the prior access device through the port, providing a passage for a surgical object to access the patient's body. Typically, the cannula includes respective proximal and distal ends, an elongate member disposed therebetween, and a seal housing positioned at the proximal end. The elongate member defines an opening dimensioned to permit the passage of surgical object. Further, the elongate member is longer in length than that of the open-ended port. Thus, upon positioning, the distal end of the elongate member of the cannula reaches beyond the distal end of the open-ended port and extends into the patient's body cavity. Furthermore, the seal housing of the cannula is adapted to receive the surgical object inserted through the elongate member so as to form a substantially fluid-tight seal with the surgical object. Because the diameter of the seal housing is substantially larger than the diameter of the open-ended port, the seal housing is thus inhibited from entering the open-ended port. Therefore, upon positioning, the seal housing is positioned outside the access device, e.g. positioned above the opening of the open-ended port. Further, the cannula includes a closure valve which is normally closed in the absence of a surgical instrument. The closure valve thus inhibits gas leakage and introduction of foreign matter in its closed state, therefore serving as a complement to the open-ended ports.

In the prior art, during the operation of the access device, a surgeon introduces the access device into the incision either before or after introducing insufflation gas into the surgical site. After placing the prior access device into the incision, the surgeon inserts a cannula into each open-ended port of the access device, and then inserts a surgical instrument into each cannula. In multiple port access devices, cannulas are often staggered relative to the access device to facilitate movement of the surgical instruments. When multiple cannulas are positioned within the access device concurrently, the seal housings of the cannulas are all positioned above the access device. The seal housings may clash against each other as the surgeon manipulates multiple surgical instruments that are inserted through the multiple cannulas simultaneously. The collisions among the seal housings not only cause great interference with the movements of the surgical instruments, but also limit the number of cannulas that can coexist within an access device of a given size, thereby reducing the number of surgical instruments that can simultaneously operate through the access device. Similarly, the distal ends of the cannulas, which are positioned inside the patient's body cavity, may also cause interference with the instrument motion, as the distal ends of the cannulas clash within the body cavity. Further, in the prior art, the surgical instruments that are inserted through a single access port via cannulas have a limited freedom of movement constrained by the physical characteristics of the cannulas and the open-ended ports. For instance, an open-ended port provides an open channel in a longitudinal direction of the access port. For that reason, the elongate member of the cannula, when positioned within the open-ended port, provides a channel for the surgical instruments to maneuver in a longitudinal direction relative to the access port. However, to reach a desired operation site within the patient's body cavity, the surgeon often needs to move the surgical instrument in a slanting or sloping direction relative to the access port.

Thus, to facilitate and provide greater freedom of movement of the surgical instruments and to avoid potential interferences therewith, a continuing need exists for an access device with enhanced sealing features and enhanced port features.

SUMMARY

The present disclosure pertains to a surgical apparatus that includes a seal anchor member. The seal anchor member includes a first end, a second end, at least one longitudinal port extending between the two ends, and a seal assembly disposed within the at least one longitudinal port. The seal assembly comprises a seal housing which is configured to receive a surgical instrument inserted into the at least one longitudinal port and form a substantially fluid-tight seal therewith, thereby inhibiting the loss of insufflation gas between the at least one longitudinal port and the surgical instrument, thus precluding the need of a separate cannula. The seal assembly further comprises a closure valve which inhibits the escape of insufflation gas from the underlying peritoneal cavity of the patient, in the absence of the surgical instrument.

In one embodiment, the seal assembly is an integrated part of the seal anchor member. The seal assembly and the remaining parts of the seal anchor member are formed in one piece. Alternatively, the seal assembly is permanently attached to the remaining portion of the seal anchor member by glue or by an overmolding process.

In another embodiment, the seal assembly is detachably connected to the remaining parts of the seal anchor member. The seal assembly can be adjusted to various positions along the length of the at least one longitudinal port. The seal assembly can be securely engaged with the at least one longitudinal port through frictional engagement.

In a third embodiment, the seal anchor member comprises a plurality of longitudinal ports and a plurality of seal assemblies, each seal assembly being disposed in one of the plurality of longitudinal ports. Each seal assembly is positioned at a different elevation with respect to the height of the seal anchor member, thereby minimizing lateral interferences that could occur between adjacent seal assemblies.

In a fourth embodiment, the seal anchor member further comprises a protective sleeve disposed on an inner surface of the at least one longitudinal port along the length thereof. The protective sleeve protects the inner surface of the longitudinal port from accidental penetration by the surgical instruments as the surgical instruments insert through the seal anchor member. The protective sleeve may include a layer of coating made of a non-stick, lubricant material on its inner surface to reduce friction between the protective sleeve and the surgical instruments.

In a fifth embodiment, the seal anchor member comprises a seal assembly that includes a pivotable member to pivot the surgical instrument inserted therein with respect to a longitudinal axis of the seal anchor member, thereby facilitating the surgical instrument to move in a slanting or sloping direction (e.g., an off-axis direction with respect to the longitudinal axis).

In addition, while certain aspects of this disclosure are described as relating to laparoscopic surgery via the abdominal wall, it should be understood that the present invention is equally relevant to, and may be employed in connection with, other types of surgery such as incision-less surgery, whereby access to a body cavity is provided via a natural orifice such as the vagina, anus, mouth, ear, nasal passage, etc.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
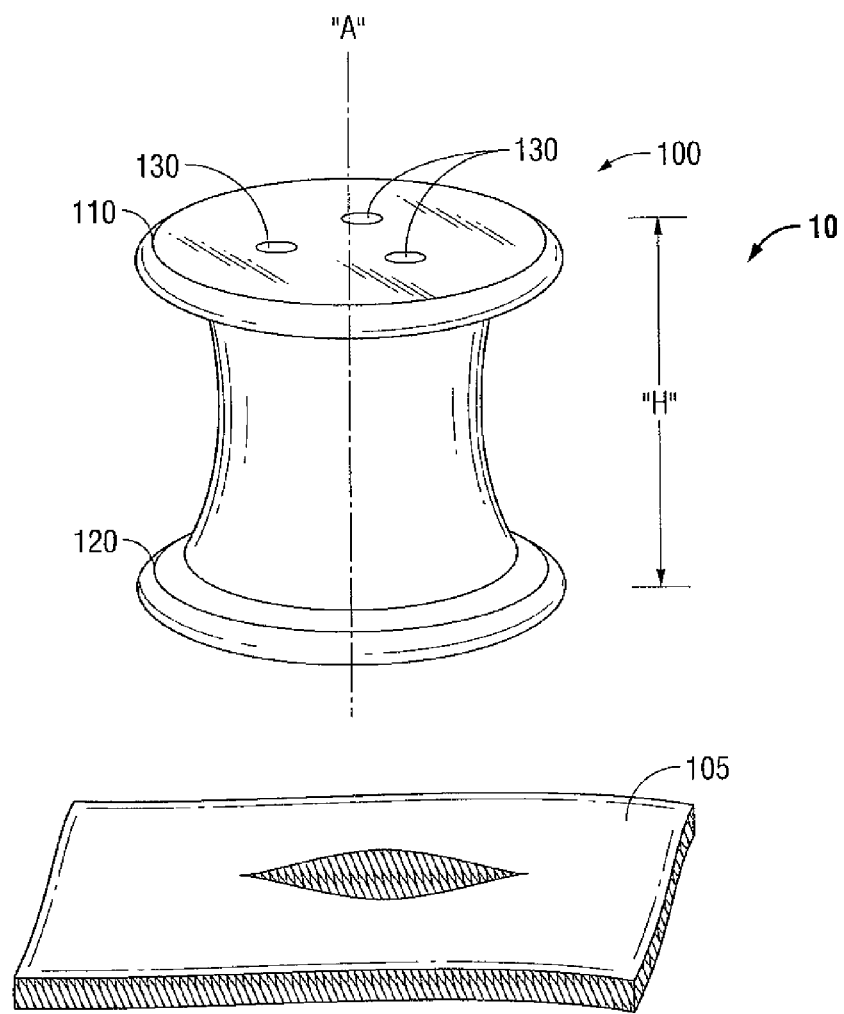
FIG. 1 is a perspective view of a surgical apparatus in accordance with the principles of the present disclosure.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein employs a device that facilitates multiple instrument access through a single incision. This is a minimally invasive surgical procedure, which permits a surgeon to operate through a single entry point, typically the patient's navel. The disclosed procedure involves insufflating the peritoneal cavity and positioning a portal member within, e.g., the navel of the patient. Instruments including an endoscope and additional instruments such as graspers, staplers, forceps or the like may be introduced within the portal member to carry out the surgical procedure. An example of such a surgical portal is disclosed in commonly assigned U.S. patent application Ser. No. 12/244,024, filed Oct. 2, 2008, published as U.S. Patent Publication 2009/0093752, the entire contents of which are hereby incorporated by reference herein.

Referring now to the drawings, in which like reference numerals identify identical or substantially similar parts throughout the several views, FIG. 1 illustrates a surgical apparatus 10 including a seal anchor member 100 which is adapted for insertion within a tissue tract 105, e.g., through the abdominal or peritoneal lining in connection with a laparoscopic surgical procedure.

With continued reference to FIG. 1, the seal anchor member 100 has a proximal end 110 and a distal end 120. The seal anchor member 100 further comprises at least one longitudinal port 130 extending along a longitudinal axis "A" of the seal anchor member 100 between its proximal end 110 and its distal end 120. The seal anchor member 100 also defines a height "H" corresponding to the linear distance between the proximal end 110 and the distal end 120 along the longitudinal axis "A." The longitudinal ports 130 are dimensioned to receive surgical objects (not shown) therethrough. Suitable surgical objects to be introduced within one or more of the ports 130 include minimally invasive grasper instruments, forceps, clip-appliers, staplers, etc. Seal anchor member 100 may define an hourglass shape as shown. Proximal and distal ends 110, 120 may define flange segments, which may be integrally formed with seal anchor member 100. Seal anchor member 100 may be made from a rigid or semi-rigid material. Seal anchor member 100 may also be made from a resilient, disposable, compressible, and/or flexible type material, for example, but not limited to, a suitable foam, gel material, or soft rubber having sufficient compliance to form a seal about one or more surgical objects, and also establish a sealing relation with tissue. In one embodiment, the foam includes a polyisoprene material. Seal anchor member 100 is preferably sufficiently compliant to accommodate off axis motion of the surgical object. Additionally, due to its compliant nature, seal anchor member 100 allows curved surgical instruments to be inserted therethrough.

Figure 2:
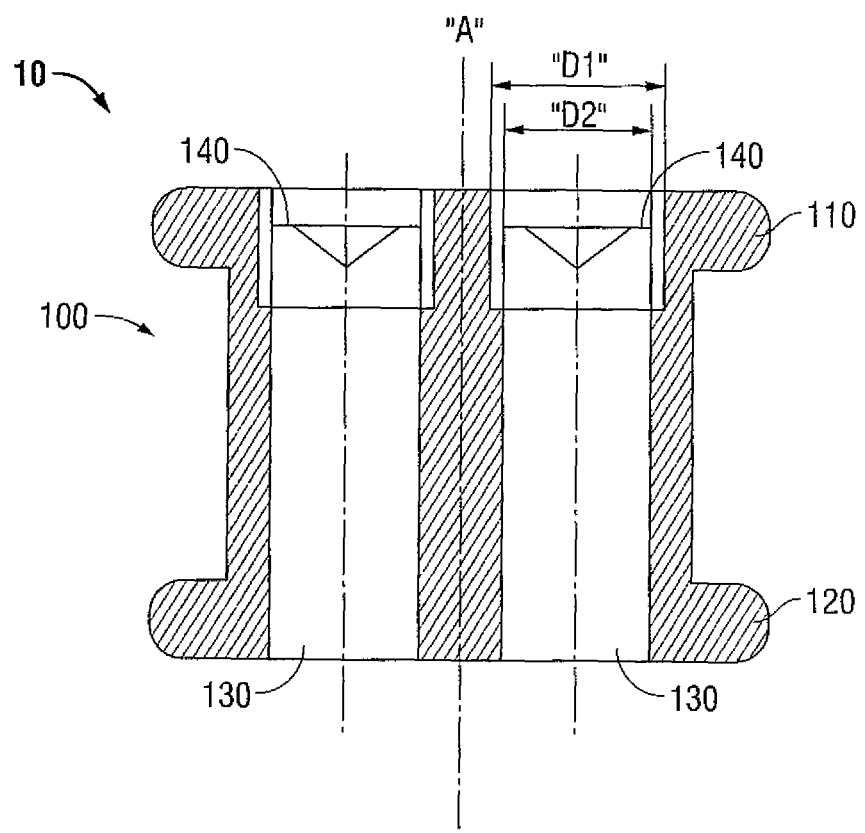
FIG. 2 is a schematic, cross-sectional view of the surgical apparatus of FIG. 1 illustrating a plurality of longitudinal ports and a seal assembly being disposed in each of the plurality of longitudinal ports.
Figure 3:
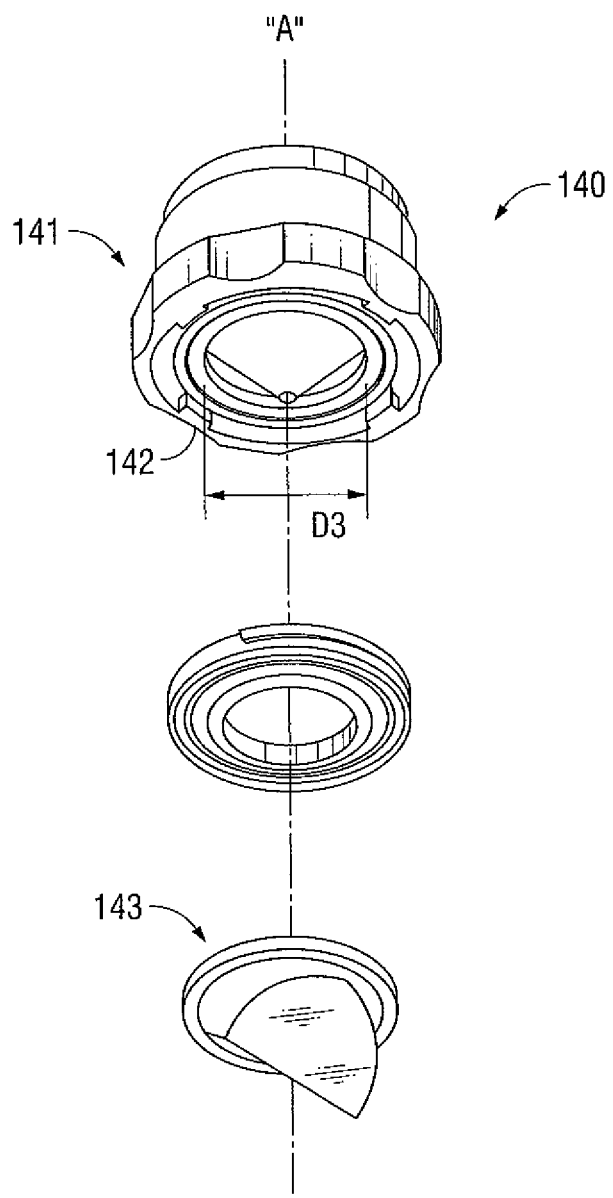
FIG. 3 is an exploded perspective view of the seal assembly of FIG. 2.

With reference to FIG. 2, the seal anchor member 100 comprises two longitudinal ports 130 each having a seal assembly 140 disposed therein at the proximal end 110 of the seal anchor member 100. Each seal assembly 140 is configured for sealed reception of a surgical instrument therethrough and includes a seal housing 141 and a closure valve 143 as depicted in FIG. 3. The seal housing 141 is designed to seal with a surgical instrument inserted therein during minimally invasive procedures.

In one embodiment, the seal assembly 140 forms an integrated part of the seal anchor member 100, such that the seal assembly 140 and the remaining parts of the seal anchor member 100 are formed in one piece produced by the same assembly process. Alternatively, the seal assembly 140 and remaining parts of the seal anchor member 100 are produced by different assembly processes, and they are later attached together by glue or by an overmolding process.

In another embodiment, the seal assembly 140 is detachably connected to the seal anchor member 100 such that the seal assembly 140 can move along the length of the longitudinal port 130 or be removed from the longitudinal port 130 completely. In one example, the seal assembly 140 has a relatively larger radial dimension than that of the longitudinal port 130. As illustrated in FIG. 2, the seal assembly 140 defines an outer diameter "D1," whereas the longitudinal port 130 defines a relatively smaller inner diameter "D2." Due to the resilient nature of the seal anchor member 100, the longitudinal port can be rendered to permit insertion of the seal assembly 140. The longitudinal port 130 is sufficiently compliant to expand its inner diameter "D2" upon insertion of the seal assembly 140 therein, forming a substantially fluid-tight seal with the seal assembly 140, and securely engaging the seal assembly 140 through frictional engagement. The seal assembly 140 can be manually adjusted to any location along the length of the longitudinal port 130 by pushing or pulling the seal assembly 140 along the length of the longitudinal port 130. Once the seal assembly 140 reaches a desired location, it then again securely engages an inner wall of the longitudinal port 130 through frictional engagement.

In a preferred embodiment as illustrated in FIG. 3, disposed within the seal housing 141 is an instrument seal 142 that is configured to receive the surgical instrument inserted into the longitudinal port 130. In one embodiment, the instrument seal 142 is made of a resilient and flexible material similar to that of the seal anchor member 100. As the surgical instrument enters the longitudinal port 130, the surgical instrument advances through the seal housing 141. Due to the resilient nature of the material that the instrument seal 142 is made of, as the surgical instrument advances through the seal housing 141, the instrument seal 142 expands to admit the surgical instrument. Further, the instrument seal 142 in its expanded state forms a substantially fluid-tight seal with the surgical instrument, thus establishing a substantially sealed relation with the surgical instrument. As the surgical instrument leaves the seal housing 141 upon removal, the instrument seal 142 contracts back to its original shape.

With continued reference to FIG. 3, the closure valve 143 is normally biased towards a closed position in the absence of a surgical instrument, and is configured to open upon the introduction of the surgical instrument inserted into the longitudinal port 130 to allow the surgical instrument to pass therethrough. During a minimally invasive procedure, after the seal anchor member 100 is inserted within a tissue tract 105 and before the surgical instrument is inserted into the seal anchor member 100, the closure valve 143 serves the purpose of closing the longitudinal port 130, thereby inhibiting the escape of the insufflation gas from the patient's peritoneal cavity, and thus inhibiting the deflation or collapse of the enlarged surgical site. For the same reason, the closure valve 143 also inhibits foreign matter from inadvertently entering into the patient's peritoneal cavity.

Further, the seal assembly 140 defines an inner diameter "D3." The inner diameter "D3" is configurable to any size, thereby permitting reception of any surgical instrument no greater than the size of the seal assembly 140 in diameter. In one embodiment, the inner diameter "D3" of the seal assembly 140 is about 5 mm. In another embodiment, the inner diameter "D3" of the seal assembly 140 is between about 5 mm and about 12 mm.

Figure 4:
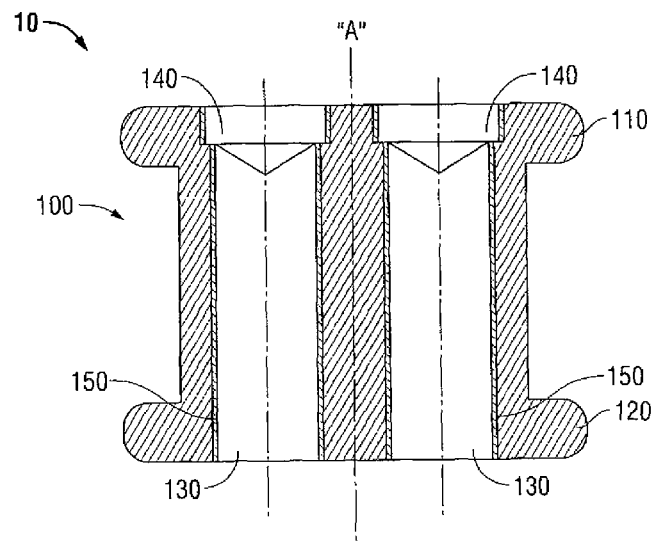
FIG. 4 is a schematic, cross-sectional view of the surgical apparatus of FIG. 1 illustrating a protective sleeve being disposed within an inner surface of each of the plurality of longitudinal ports.

With reference to FIG. 4, the seal assembly 140 may further comprise a protective sleeve 150 disposed on an inner surface of the longitudinal port 130 along the length of the longitudinal port 130. The protective sleeve 150 serves as an intermediate layer between the longitudinal port 130 and the surgical instrument, and acts as a guide for the surgical instrument through the longitudinal port 130. The protective sleeve 150 prevents direct contact between the longitudinal port 130 and the surgical instrument. As a result, the protective sleeve 150 protects the longitudinal port 130 from accidental penetration by the surgical instrument as the surgical instrument advances through the seal anchor member 100. The protective sleeve 150 is made of a flexible or semi-flexible material similar to that of the seal anchor member 100. To facilitate smooth movement of the surgical instrument through the protective sleeve 150, the protective sleeve 150 may additionally include a layer of coating made of a non-stick, lubricant material, thus reducing friction between the contact surfaces of the protective sleeve 140 and the surgical instrument. In one embodiment, the protective sleeve 150 is permanently attached to the inner surface of the longitudinal port 130 by glue or by an overmolding process. In another embodiment, the protective sleeve 150 is removably connected to the inner surface of the longitudinal port 130, such that the protective sleeve 150 can be slid on or off the longitudinal port 130. In that scenario, the protective sleeve 150 can be secured to the inner surface of the longitudinal port 130 through frictional engagement.

Figure 5:
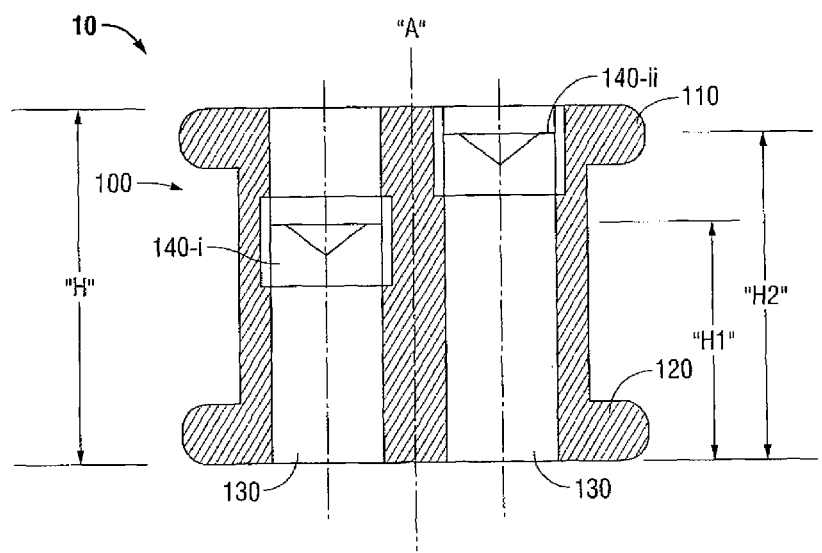
FIG. 5 is a schematic, cross-sectional view of the surgical apparatus of FIG. 1 illustrating two seal assemblies of FIG. 2 with each being disposed at a different elevation relative to the height of the surgical apparatus of FIG. 1.
Figure 6:
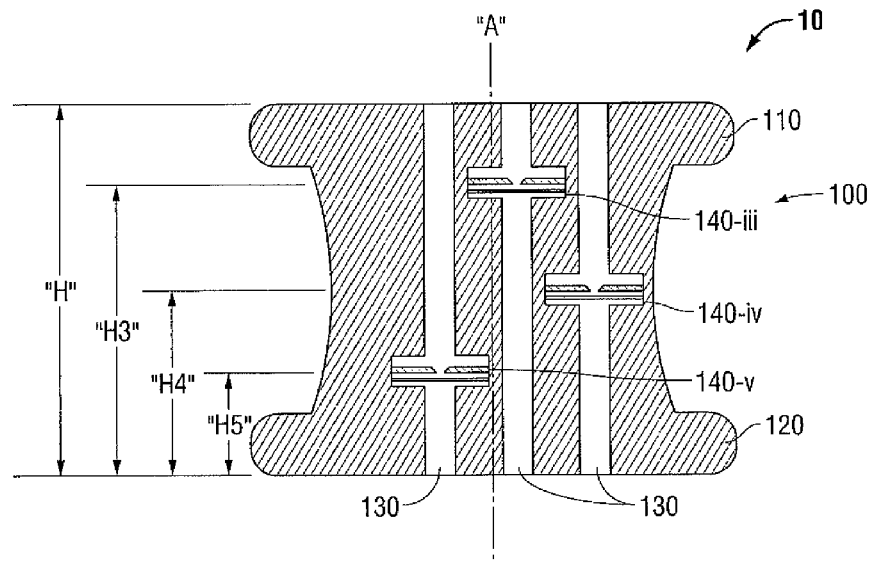
FIG. 6 is a schematic, cross-sectional view of the surgical apparatus of FIG. 1 illustrating three seal assemblies of FIG. 2, each assembly being disposed at a different elevation relative to the height of the surgical apparatus of FIG. 1.

With reference to FIG. 5, each seal assembly is positioned at a different elevation with respect to the height of the seal anchor member 100. For instance, seal assembly 140-*i* is positioned at an elevation "H1", whereas seal assembly 140-*ii* is positioned at another elevation "H2." Another similar example is provided in FIG. 6 illustrating three seal assemblies 140-*iii*, 140-*iv*, 140-*v*, each being positioned at an elevation "H3," "H4," and "H5," respectively. As explained earlier, each seal assembly has a larger radial dimension than that of the longitudinal port 130. Thus, a seal anchor member 100 that defines n longitudinal ports may not be able to accommodate n seal assemblies simultaneously at the same elevation level, e.g., at the proximal end of the seal anchor member 100 as illustrated in FIG. 2, thereby precluding n surgical instruments to be operated simultaneously. Even if the seal anchor member 100 is dimensioned to accommodate n seal assemblies simultaneously at the same elevation level, the n seal assemblies may cause lateral interferences among themselves as the surgeon manipulates n surgical instruments therethrough, thereby interfering with the surgical operation. By having seal assemblies disposed at different elevations as illustrated in FIGS. 5 and 6, the seal anchor member 100 can thus accommodate n seal assemblies simultaneously, and eliminate lateral collisions among the seal assemblies.

Figure 7:
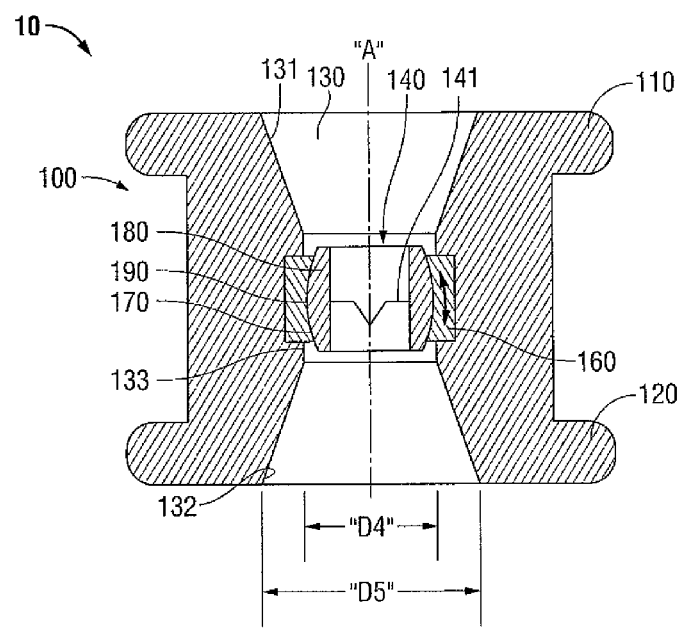
FIG. 7 is a schematic, cross-sectional view of the surgical apparatus of FIG. 1 illustrating a seal assembly comprising a pivotable inner member, and also showing a longitudinal port having a proximal and distal end each exhibiting a conical configuration.
Figure 7A:
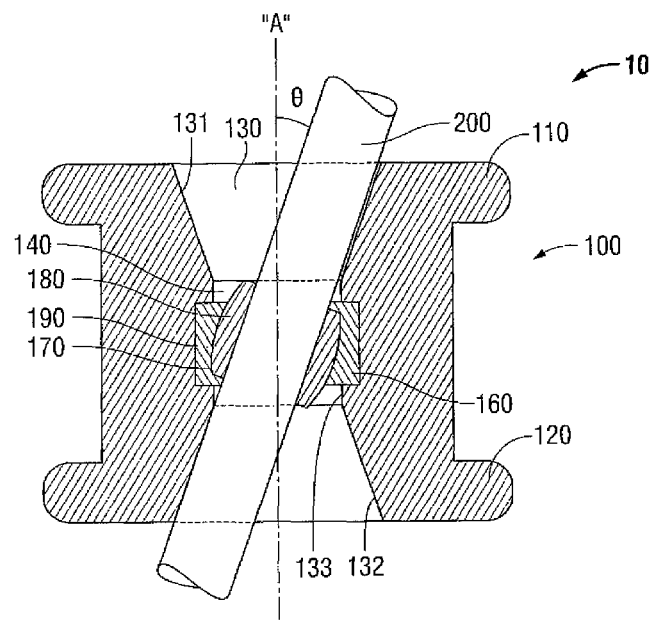
FIG. 7A-B are schematic, cross-sectional views of the surgical apparatus of FIG. 7 illustrating a surgical instrument inserted therein being pivoted with respect to the longitudinal axis of the surgical apparatus.
Figure 7B:
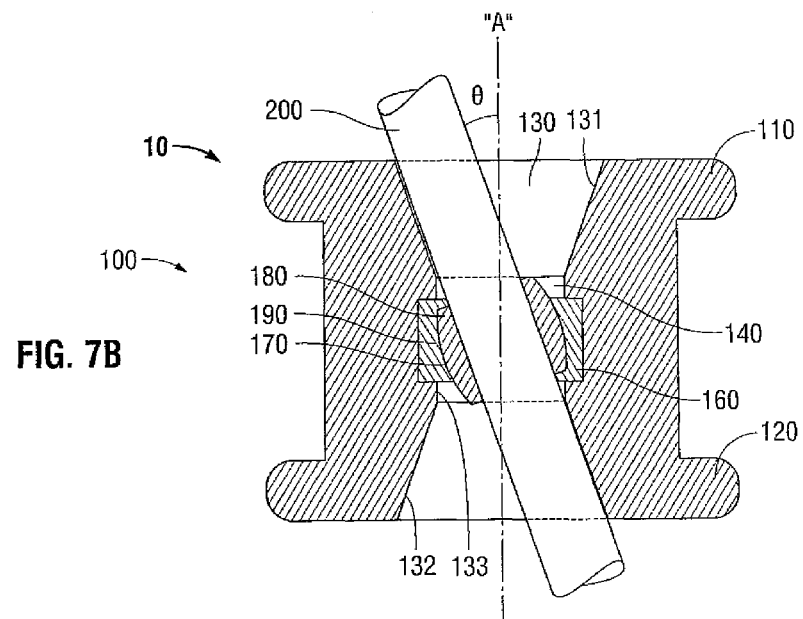

With reference to FIGS. 7, 7A and 7B, a seal assembly 140 comprises an outer member 160 and an inner member 180 that are spherically connected. The outer member 160 can be permanently affixed to the inner surface of the longitudinal port 130 by glue or by an overmolding process. Alternatively, the outer member 160 may be removably connected to the longitudinal port 130 through frictional engagement. The outer member 160 defines an inner wall 170 exhibiting a spherical-like or concave configuration. The inner member 180 defines an outer wall 190 exhibiting a spherical-like or convex configuration that complements the inner wall 170 of the outer member 160. The inner member 180 is connected to the outer member 160 through a rotation mechanism or simply by frictional engagement. Further, the inner member 180 is pivotable within the confinement of inner wall 170 of the outer member 160 to form an acute angle "θ" with respect to the longitudinal axis "A" of the seal anchor member 100. Still further, the inner member 180 is rotatable within the confinement of inner wall 170 of the outer member 160. The inner member 180 has a seal housing 141 as depicted in FIG. 3 to form a substantially fluid-tight seal with a surgical instrument inserted therein. The inner member 180 may also comprise a closure valve 143 as depicted in FIG. 3 for inhibiting the escape of the insufflation gas.

With continued reference to FIGS. 7, 7A and 7B, the longitudinal port 130 comprises a proximal portion 131, a distal portion 132 and an elongate member 133 extending between the proximal and distal portions. The elongate member 133 defines a uniform diameter "D4" through its length. Each of the proximal portion 131 and the distal portion 132 exhibits a conical configuration. For instance, as illustrated in FIG. 7, the distal portion 132 defines a radial dimension that grows gradually larger from its adjacency with the elongate member 133, measured at "D4," towards a distal-most end of the distal portion 132, measured at "D5." Likewise, the proximal portion 131 shares the same configuration as that of the distal portion 132.

As illustrated in FIGS. 7A-7B, a surgical instrument 200 can be inserted through the longitudinal port 130 and forming a substantially sealed relation with the seal assembly 140. The surgical instrument 200 can pivot or move off-axis with respect to the longitudinal axis "A" of the seal anchor member 100, through a pivotal motion of the inner member 180 of the seal assembly 140. As shown in FIGS. 7A-7B, the surgical instrument 200 forms an acute angle "θ" with respect to the longitudinal axis "A." The surgical instrument 200 can also rotate with respect to the longitudinal axis "A" of the seal anchor member 100 through a rotational motion of the inner member 180 of the seal assembly 140. Thus, by this configuration, any surgical instrument inserted within the seal assembly 140 can be easily manipulated in a slanting or sloping direction, oblique to the longitudinal axis "A" of the seal anchor member 100, as necessary to appropriately engage tissue within the patient's body cavity. The surgical instrument can also be easily manipulated to rotate relative to the longitudinal axis "A" of the seal anchor member 100, or manipulated to engage in an off-axis rotation in the slanting or sloping direction, oblique to the longitudinal axis "A."

The seal anchor member 100 of the present disclosure precludes the need a separate cannula assembly, because the seal assembly 140 disposed within the seal anchor member 100 is capable of forming fluid-tight seals with surgical instruments and inhibiting insufflation gas leakage which is normally done by the separate cannula assembly.

In use, the freedom of movement of the surgical instruments is greatly increased. Potential interferences with the instruments motion are substantially reduced by disposing seal assemblies 140 within the longitudinal ports 130, thus avoiding collisions that otherwise would occur when using cannulas. Further, because the present disclosure obviates the needs of a separate cannula assembly, clashes among the distal ends of cannulas are avoided. Further, by positioning multiple seal assemblies at different elevations within the seal anchor member, multiple instruments can simultaneously operate through the seal anchor member with a negligible degree of interferences among each other. Still further, the surgical instrument can easily move in off-axis directions through motion of the seal assemblies. Hence, the present disclosure provides increased latitude for instrument motion.

Furthermore, the surgical instruments of various shapes, such as curved surgical instruments, can be inserted into the seal anchor member 100, without requiring any particular shape.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical apparatus for positioning within a tissue tract accessing an underlying body cavity, which comprises:
   a seal anchor member comprising a first end, a second end, and at least two longitudinal ports extending between the first and second ends, each longitudinal port of the at least two longitudinal ports defining a proximal end and a distal end; and
   at least two seal assemblies configured for substantially sealed reception of an object therein, a first seal assembly of the at least two seal assemblies disposed within a first longitudinal port of the at least two longitudinal ports and positioned at a first distance from the proximal end of the first longitudinal port, and a second seal assembly of the at least two seal assemblies disposed within a second longitudinal port of the at least two longitudinal ports and positioned at a second distance from the proximal end of the second longitudinal port, the first distance being different than the second distance, wherein the first and second seal assemblies are selectively movable from the proximal to the distal ends of the respective first and second longitudinal ports.

2. The surgical apparatus according to claim 1, wherein each seal assembly of the at least two seal assemblies comprises a seal housing for receiving the object and forming a substantially fluid-tight seal therewith.

3. The surgical apparatus according to claim 1, wherein each seal assembly of the at least two seal assemblies comprises a closure valve configured to inhibit communicating insufflation gas therethrough.

4. The surgical apparatus according to claim 1, wherein each seal assembly of the first seal assembly and the second seal assembly defines a radial diameter larger than a respective radial diameter of the first longitudinal port and the second longitudinal port.

5. The surgical apparatus according to claim 1, wherein at least one longitudinal port of the at least two longitudinal ports includes a seal receiving cavity configured to receive one seal assembly of the at least two seal assemblies therein, the seal receiving cavity oriented transverse to a longitudinal axis of the at least one longitudinal port.

6. The surgical apparatus according to claim 1, wherein the first and second longitudinal ports define first and second longitudinal axes, respectively, the first and second longitudinal axes being non-collinear.

* * * * *